United States Patent [19]
Hoglen et al.

[11] Patent Number: 5,721,364
[45] Date of Patent: Feb. 24, 1998

[54] PROCESS FOR MAKING 2-AMINO-4, 6-DIALKOXY-1, 3, 5-TRIAZINES

[75] Inventors: Dean Kent Hoglen; Heinz Peter Schwemlein; Herng-Tay Wu, all of Baton Rouge, La.

[73] Assignee: Novartis Corporation, Summit, N.J.

[21] Appl. No.: 767,265

[22] Filed: Dec. 13, 1996

[51] Int. Cl.$^6$ .................. C07D 251/44; C07D 251/46
[52] U.S. Cl. .............................. 544/219; 544/217
[58] Field of Search ................................ 544/217, 219

[56] References Cited

U.S. PATENT DOCUMENTS 4,479,821  10/1984  Meyer et al. ...................... 544/211

OTHER PUBLICATIONS

E.M. Smolin et al, "s–Triazines and Derivatives," Chapter V, pp. 274–281, of Interscience Publishers Inc., NY (1959).
Dudley et al., JACS, Jul. 6, 1951, vol. 73, pp. 2990–2992.

*Primary Examiner*—John M. Ford
*Attorney, Agent, or Firm*—William A. Teoli, Jr.

[57] ABSTRACT

A method is provided for making ammelide ethers, such as a 2-amino-4,6-dialkoxy-1,3,5-triazine. A 2-amino-4,6-dihalo-1,3,5-triazine (ADXT) is synthesized in the presence of an aromatic organic solvent, and reaction is effected directly between the (ADXT) synthesis mixture and an alkali metal $C_{(1-4)}$alkoxide and $C_{(1-4)}$alkanol, including contact through a static mixer. These ammelide ethers are useful as intermediates for making N-phenylsulfonyl-N-triazinylureas, which have herbicidal and growth regulating properties.

13 Claims, No Drawings

PROCESS FOR MAKING 2-AMINO-4, 6-DIALKOXY-1, 3, 5-TRIAZINES

BACKGROUND OF THE INVENTION

1. Field of the Invention

The present invention relates to a method for making ammelide ethers, such as 2-amino-4,6-dialkoxy-1,3,5-triazines. More particularly, the present invention relates to a method involving the initial synthesis of a 2-amino-4,6-dialkoxy-1,3,5-triazines by effecting reaction in the presence of an aromatic organic solvent and under substantially anhydrous conditions between ammonia and a 2,4,6-trihalo-triazine; thereafter, the 2-amino-4,6-dihalo-1,3,5,-triazine reaction mixture is combined directly with an alkanol and an alkali metal alkoxide, such as sodium methoxide, to provide for the formation of the ammelide ether.

2. Discussion of the Prior Art

Ammelide (2-amino-s-triazine-4,6-diol) is known. As disclosed in Meyer et al, U.S. Pat. No. 4,479,821, ammelide ethers, such as 2-amino-4,6-dialkoxy-1,3,5-triazines are valuable as intermediates in the synthesis of N-phenylsulfonyl-N-triazinylureas, which have herbicidal and growth-regulating properties.

As reported by E. M. Smolin et al in "s-Triazines and Derivatives," Chapter V, page 274, of Interscience Publishers Inc., N.Y. (1959), ammelide ethers were prepared by Hofmann et al, by reacting ammonia with trialkyl cyanurates. Additional procedures for making ammelide ethers which are discussed involve the addition of 2-amino-4,6-dichloro-s-triazines to a suspension of sodium hydroxide in the desired alcohol.

E. M. Smolin et al also show techniques on pages 279–81, for preparing ammelide ether precursors, such as 2-amino-4,6-dichloro-s-triazine by reacting cyanuric chloride, with ammonia or an amine. Diethyl ether, or dioxane can be used to facilitate reaction between ammonia and cyanuric chloride. The reaction between ammonia and cyanuric chloride also can be effected at about −40° C. to about 8° C. under anhydrous or aqueous conditions, depending upon the solvent used.

Further methods for making ammelide ethers are shown by Dudley et al JACS, Jul. 6, 1951, vol. 73, page 2989, whereby the appropriate 2-amino-4,6-dichloro-s-triazine is added directly to a solution of sodium hydroxide in the selected alcohol.

As shown by the prior art, a variety of techniques are available for making ammelide ethers, particularly reactions involving the use of ammelide ether precursors such as 2-amino-4,6-dichloro-s-triazine.

SUMMARY OF THE INVENTION

Even though a number of techniques are available for making ammelide ethers, or precursors thereof, new procedures are constantly being evaluated. It would be desirable, for example, to make ammelide ethers by a "one pot reaction", or variation thereof, starting with the cyanuric halide source material instead of the 2-amino-4,6-dihalo-1,3,5-triazine (ADXT) precursor. In a one pot reaction, a $C_{(1-4)}$alkanol, such as methanol, and an alkali metal alkoxide, for example sodium methoxide, would be added directly into a reaction mixture of cyanuric chloride and ammonia, in place of the 2-amino-4,6-dichloro-s-triazine precursor. It would be a significant advantage to be able to make ammelide ethers starting with cyanuric chloride (CC), instead of having to isolate the 2-amino-4,6-dichloro-s-triazine precursor, or avoid having to exchange the solvent, prior to the final recovery of the ammelide ether.

However, a possible risk of using the "one pot" procedure for making ammelide ethers is that an unwanted build-up in the concentration of undesirable by-products, such as diaminotriazine might occur due to the generation of an extra equivalent of ammonia during the synthesis of the aminodichlorotriazine (ADCT) precursor. For example, a build-up of diaminotriazine might be expected from the ammonium chloride containing ADCT reaction mixture if it were directly treated with an alkali metal alkoxide.

Unexpectedly, it was found that ammelide ethers in fact can be made directly by the one pot procedure in high yields while avoiding a build-up in unwanted by-products. Accordingly, the isolation of a product intermediate, or the exchange of solvent prior to final product recovery can be avoided, if the mixture of alkali metal alkoxide and alkanol is added directly to the ADCT reaction mixture prepared by reacting ammonia or an amine with cyanuric halide in an aromatic organic solvent, such as toluene, as shown by the following equations:

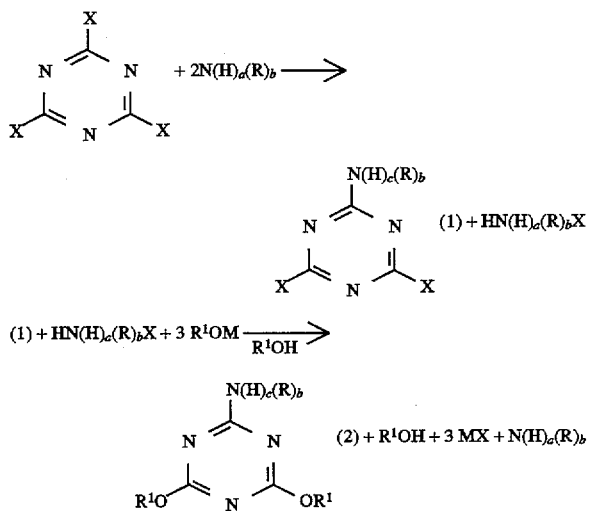

where X is a halogen radical; R is a straight-chain or branched $C_{(1-4)}$alkyl radical; each $R^1$, independently of the other, is selected from the group consisting of a straight-chain or branched $C_{(1-4)}$alkyl radical and a straight-chain or branched $C_{(1-4)}$alkoxyalkyl radical; M is an alkali metal ion; a is an integer equal to 2 or 3, b is a whole number equal to 0 or 1, and the sum of a+b is equal to 3; c is an integer equal to 1 or 2, and the sum of b+c is equal to 2.

Surprisingly, the reaction mixture of the ammelide ether, for example aminodimethoxytriazine (ADMT), prior to final recovery, has been found to have less than 0.5% diaminotriazine. It was further found that the use of a static mixer, which provides mixing by fluid motion, as the result of the use of tubular equipment having helical elements to impart an alternate left and right twist, has been found to be especially useful in large scale operations. Especially valuable results are achieved with the use of a static mixer to achieve static blending of the respective aminodichlorotriazine mixture, and the alkali metal alkoxide and alkanol mixture, which respectively can be separately and concurrently fed into the static mixer prior to being discharged into a vessel to contain the final ADMT reaction mixture.

STATEMENT OF THE INVENTION

There is provided by the present invention, a process for making ammelide ethers which comprises the steps of:

(a) forming a first mixture comprising a 2-amino-4,6-dihalotriazine (ADXT) by effecting reaction in the presence of an aromatic organic solvent, and under substantially anhydrous conditions, between the components in a mixture comprising, a cyanuric halide and a hydronitrogen compound selected from the group consisting of ammonia and a $C_{(1-4)}$alkyl amine, where the (ADXT) has the formula,

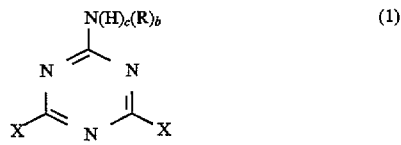

(1)

and, (b) effecting reaction under substantially anhydrous conditions, between the components of the (ADXT) mixture of (a), and the components of a mixture comprising a $C_{(1-4)}$alkanol and an alkali metal $C_{(1-4)}$ alkoxide, to form a 2-amino-4,6-dialkoxy-1,3,5-triazine (AD(OR)T) ammelide ether of the formula,

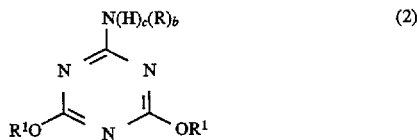

(2)

where X, R and $R^1$, b and c are as previously defined.

DETAILED DESCRIPTION OF THE INVENTION

Radicals included within R and $R^1$ of formulas (1) and (2) are for example straight-chain or branched $C_{(1-4)}$alkyl, such methyl, ethyl, n-propyl, isopropyl, and the four isomers of butyl, with straight-chain $C_{(1-4)}$alkyl being preferred; radicals included within X are for example, chloro, which is preferred, and bromo and iodo; alkali metal ions included within M are for example sodium, potassium and lithium; other radicals included within $R^1$ are for example straight-chain or branched alkoxyalkyl of at most 4 carbon atoms.

In addition to ammonia, the hydronitrogen compound can include alkyl amines such as, methylamine, ethylamine, propylamine, isoproylamine and the four isomeric butylamines, $C_{(1-4)}$alkanols which can be used in the practice of the invention are for example methanol, ethanol, propanol, isopropanol, the four isomeric butanols, and alkoxyalkanols such as ethylene glycol monomethyl ether. Suitable alkali metal $C_{(1-4)}$alkoxides correspond to the listed $C_{(1-4)}$alkanols in which the H of the hydroxyl group is replaced by sodium, potassium or lithium.

In the practice of the invention, the ADXT is initially prepared by agitating a mixture of the cyanuric halide, for example, cyanuric chloride, and the hydronitrogen compound in the presence of an organic solvent at temperatures in the range of 0° C. to 50° C. under substantially anhydrous conditions. The organic solvent is preferably a $C_{(6-10)}$ aromatic organic solvent, which includes alkylaromatic, and haloaromatic solvents which are liquid at 0° C. to 90° C.; most preferred are $C_{(6-10)}$ aromatic organic solvents, such as benzene, toluene, and the xylenes, while toluene is particularly preferred.

Reaction time for preparing the ADXT can vary from as little as several minutes to several hours depending upon the scale of the reaction and the conditions used.

In the preparation of the 2-amino-4,6-dialkoxy-1,3,5-triazine (AD(OR)T), the $C_{(1-4)}$alkanol can be initially added to the ADXT reaction mixture, followed by the subsequent addition in several stages (for example, one or two stages) of additional $C_{(1-4)}$alkanol in combination with the alkali metal alkoxide, at temperatures in the range of 0° C. to 70° C. Alternatively, the AD(OR)T of formula (2) is formed by adding the mixture comprising the $C_{(1-4)}$alkanol and the alkali metal $C_{(1-4)}$alkoxide directly into the ADXT reaction mixture, while the temperature is maintained at about 55° C. to about 65° C. The total $C_{(1-4)}$alkanol charge can vary widely, such as from 0 to up to about 10 (or more) times the weight, or higher depending upon the cyanuric halide used, and the molecular weight of the $C_{(1-4)}$alkanol. There can be used from about 3 up to about 5 moles of the alkali metal alkoxide, per mole of the cyanuric halide. Preferably, from about 3 up to about 3.5 moles of the alkali metal alkoxide is used per mole of the cyanuric halide. After the addition of the alkali metal alkoxide has been completed, the total mixture can be refluxed, or if under sealed conditions, can be heated in the range of about 20° C. to 80° C.

The preferred procedure for making the AD(OR)T, particularly in large scale reactions, such as a pilot plant or larger, is to effect concurrent contact between the ADXT reaction mixture, and the mixture of the $C_{(1-4)}$alkali metal oxide and $C_{(1-4)}$alkanol; the two respective mixtures can then be concurrently introduced from separate sources into a static mixer to achieve fluid mixing prior to being discharged into a receiving vessel. Suitable static mixers are, for example, those which have helical elements to impart an alternate left and right twist such as the Chemineer Model 2KMS2 (Chemineer Co./Dayton Ohio) which can be used for large scale reactions (such as a Pilot Plant, etc.). Since the reaction is exothermic, care must be taken to introduce the two respective mixtures into the reactor at a rate sufficient to maintain control of the reaction and thereby avoid undesired overheating and/or loss of solvent.

If desired, a surfactant can be employed to facilitate separation of salts from the final product at recovery. For example, a surfactant can be added to the receiving vessel prior to or during the concurrent introduction of (i) the ADXT reaction mixture and (ii) the mixture of the $C_{(1-4)}$ alkali metal oxide and $C_{(1-4)}$alkanol into the static mixer. Alternatively, a surfactant can be added during a water quenching step at final workup.

Final workup can be achieved by filtration and addition of water at about 20° C. to about 60° C., followed by washing and drying of product.

In order that those skilled in the art will be better able to practice the present invention, the following examples are given by way of illustration and not by way of limitation. All parts are by weight unless otherwise indicated.

EXAMPLE 1

A mixture of 107 g of cyanuric chloride and 400 g of toluene are stirred at ambient temperature until a homogeneous solution is obtained. The solution is cooled to 0° C. to 10° C. which causes the precipitation of a major amount of cyanuric chloride. A total of 17 g of ammonia gas is bubbled into the heterogeneous mixture over a two hour period while maintaining the temperature between 0° C. to 10° C. There is then added 100 g of methanol to the mixture. While maintaining the temperature in the range of 0° C. to 10° C., there is added 125 g of a 25% solution of sodium methoxide in methanol over a two hour period. An additional 263 g of 25% sodium methoxide in methanol is added rapidly causing a temperature rise to 50° C. The heterogeneous mixture is then heated one hour at 50° C. to 60° C. and is transferred to a Parr reactor (an enclosed metal pressure reactor, Parr Instrument Co., Illinois). The reactor is heated two hours at 75° to 80° C. Upon cooling to 49° C., the reactor is opened; there is added 350 ml of water and an effective amount of Sandozin N surfactant (formerly available from Sandoz Corp). The mixture is stirred for three hours and filtered. After drying at 100° C., there is obtained 77.5 g, or an 85.7% yield of 2-amino-4,6-dimethoxy-1,3,5-triazine (ADMT).

EXAMPLE 2

There is added to the atmosphere above the reaction mixture 5.1 g (0.299 moles) of ammonia gas over a 25 minute period at 20° to 40° C., to a mixture of 26.8 g (0.145 moles) of cyanuric chloride and 100 g of toluene. The mixture is cooled to 10° C. and 25 g of methanol is added. There is then added over a five minute period, 99.0 g of a 25% solution of sodium methoxide to the resulting mixture causing it to reflux. The mixture is kept under reflux for 15 minutes; there is then added 100 g of water. A white solid is obtained after the mixture is filtered and washed with 50 g of water. After drying at 80° C. for several hours, 20.3 g of a white solid is obtained. Based on method of preparation, there is obtained an 85.4% yield of 2-amino-4,6-dimethoxy-1,3,5-triazine (ADMT) based on cyanuric chloride.

EXAMPLE 3

There is added to the atmosphere above the reaction mixture 5.3 g (0.311 moles) of ammonia gas over a 35 minute period at 20° to 40° C., to a mixture of 26.8 g (0.145 moles) of cyanuric chloride and 100 g of toluene. The resulting mixture, referred hereinafter as "mixture 1 ," is cooled to 10° C. A second mixture, or "mixture 2," is prepared which contained 99.5 g (0.46 moles) of sodium methoxide in methanol. There is added 10 g of methanol to mixture 1. Mixture 1 and mixture 2 are concurrently added over a 25 minute period to a common vessel which contains 10 g of methanol maintained at 60° C. A refluxing mixture results. The mixture is allowed to reflux for 15 minutes and 100 grams of water are added. There is obtained a white solid upon filtering and washing the mixture with 50 g of water. After drying at 80° C. for several hours, there is obtained 20.0 g of a white solid. The product is 94.2% ADMT, (0.121 moles), or 83.0% based on cyanuric chloride.

EXAMPLE 4

A first mixture is stirred consisting of 135.3 g (0.734 moles) of cyanuric chloride and 500 g of toluene. There is added to the atmosphere above the first mixture over a 140 minute period, 27.6 g (1.621 moles) of ammonia gas to the first mixture at 25° C. to 30° C. The first mixture is maintained at 25° C. to 30° C. for one hour, then cooled to 10° C. There is then added, 127 g of methanol to the first mixture.

A second mixture consisting of 486 g (2.249 moles) of a 25% solution of sodium methoxide in methanol, and the first mixture are simultaneously pumped into a stainless steel static mixer (Chemineer, 15 elements, ½ inch in diameter and 11⅞ inch long, mfg. by the Chemineer Co. located in Dayton Ohio) which is fed into a common vessel and refluxed for two hours. The mixture is cooled down to 45° C. and 500 g of ice water is added. The mixture is filtered and 320 g of water is used to wash the filter cake. Upon drying in a vacuum oven at 85° C., there is obtained 97 g; 94.5% (0.587 moles) of ADMT, which is 80.0% yield based on cyanuric chloride.

EXAMPLE 5

There is added to the atmosphere above the reaction mixture over a 4 to 5 hour period, 50.8 kg (2.983 k moles) of ammonia gas, while maintaining a temperature of 10° to 45° C., to a mixture of 1225 kg of a 22.3% solution of cyanuric chloride (273.1 kg; 1.481 k moles) in toluene at 45° C. There is obtained a thick reaction mass of 2-amino-4,6-dichloro-1,3,5-triazine and ammonium chloride. The mixture is cooled to 5°–10° C. and 334 kg of methanol is added. There is obtained a mixture which is referred to hereinafter as the "first mixture."

The above first mixture and a second mixture are simultaneously transferred through a Chemineer static mixer (Model 2KMS2) into a vessel containing 195 kg of methanol, 22.7 kg of a 25% (0.105 k moles) of sodium methoxide in methanol, and 0.22 kg of Geropon surfactant T22A of the Rhone Poulenc Co. The second mixture consists of 1076 kg of a 25% solution sodium methoxide (4.981 k moles) in methanol. An exothermic reaction results and the resulting mixture is kept under reflux during mixing. Ninety kg of methanol rinse solvent is combined with the reaction mass. There is distilled off 725 kg of solvent (ca. 2:1 methanol:toluene) during and after the simultaneous addition.

The resulting mixture is cooled to 60° C. and transferred to a vessel containing 985 kg of 50° C. water. After up to about two hours of mixing at 50° C., the mixture is cooled to 20° to 30° C. and transferred to a stirred pressure filter and washed with water. There is obtained 216 kg of dry ADMT (98.4%, 1.361 k moles; 91.9% yield based on cyanuric chloride).

It is further found that when methyl t-butyl ether is substituted for toluene in forming the 2-amino-4,6-dichloro-s-1,3,5-triazine, a yield of only 73.2% ADMT is achieved. One possible explanation is that the resulting reaction product, unlike toluene which forms a heterogeneous mixture, is more soluble in the ether solvent.

In summary, it is seen that this invention provides a new process for making ammelide ethers. Variations may be made in proportions, procedures and materials without departing from the scope of the invention as defined by the following claims.

What is claimed is:

1. A process for making an ammelide ether comprising the steps of, (a) forming a 2-amino-4,6-dihalotriazine (ADXT) by effecting reaction in the presence of an aromatic organic solvent, and under substantially anhydrous conditions, between the components in a mixture comprising, a cyanuric halide and a hydronitrogen compound selected from the group consisting of ammonia and a $C_{(1-4)}$alkyl amine, where the (ADXT) has the formula,

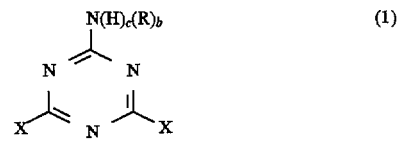

(1)

and (b) effecting reaction under substantially anhydrous conditions between the components in the (ADXT) mixture of (a), and the components in a mixture comprising a $C_{(1-4)}$alkanol and an alkali metal $C_{(1-4)}$alkoxide, whereby a 2-amino-4,6-dialkoxy-1,3,5-triazine (AD(OR)T) ammelide ether is formed having the formula,

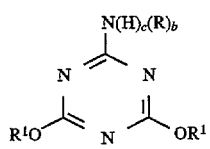

(2)

where X is a halogen radical, R and $R^1$ are respectively selected from straight-chain or branched $C_{(1-4)}$alkyl radicals, b is a whole number equal to 0 or 1, c is an integer equal to 1 or 2, and the sum of b+c is equal to 2.

2. A process in accordance with claim 1, where the ADXT of formula (1) is formed by effecting reaction at a temperature of about 0° C. to about 50° C.

3. A process in accordance with claim 1, where the AD(OR)T of formula (2) is formed by adding the mixture comprising the $C_{(1-4)}$alkanol and the alkali metal $C_{(1-4)}$ alkoxide directly into the ADXT reaction mixture, while the temperature is maintained at about 55° C. to 65° C.

4. A process in accordance with claim 1, where the AD(OR)T is formed by concurrently introducing from separate sources, the ADXT reaction mixture, and mixture comprising the $C_{(1-4)}$alkanol and alkali metal $C_{(1-4)}$alkoxide into a reactor at a rate sufficient to maintain control of the reaction.

5. A process in accordance with claim 3, where the ADXT reaction mixture and mixture comprising the $C_{(1-4)}$alkanol and alkali metal $C_{(1-4)}$alkoxide are initially contacted by being separately fed into a static mixer and thereafter, the resulting mixture is fed into a vessel.

6. A process in accordance with claim 1, where the ammelide ether is 2-amino-4,6-dimethoxy-1,3,5-triazine (ADMT).

7. A process in accordance with claim 1, where the hydronitrogen compound is ammonia.

8. A process in accordance with claim 1, where the aromatic organic solvent is toluene.

9. A process in accordance with claim 1, where the $C_{(1-4)}$alkanol is methanol.

10. A process in accordance with claim 1, where the $C_{(1-4)}$alkali alkoxide is sodium methoxide.

11. A process in accordance with claim 1, where the cyanuric halide is cyanuric chloride.

12. A process in accordance with claim 1, where the ammelide ether is formed by adding the mixture of the $C_{(1-4)}$alkanol and a $C_{(1-4)}$alkali alkoxide directly into the mixture comprising the 2-amino-4,6-dihalotriazine.

13. A process in accordance with claim 1, where the ammelide ether is formed by simultaneously effecting reaction between the components of the 2-amino-4,6-dihalotriazine reaction mixture and the $C_{(1-4)}$alkanol and a $C_{(1-4)}$alkali alkoxide mixture.

* * * * *